United States Patent [19]

Juranitch

[11] Patent Number: 4,528,843

[45] Date of Patent: Jul. 16, 1985

[54] METHOD FOR TESTING THE SHARPNESS VALUE OF A CUTTING EDGE AND APPARATUS THEREFOR

[75] Inventor: John C. Juranitch, Ely, Minn.

[73] Assignee: Juranitch, Inc., Ely, Minn.

[21] Appl. No.: 502,676

[22] Filed: Jun. 9, 1983

[51] Int. Cl.³ .................... G01M 19/00; G01N 19/08
[52] U.S. Cl. .................................................... 73/104
[58] Field of Search ........................................ 73/104

[56] References Cited

U.S. PATENT DOCUMENTS 3,931,732 1/1976 Heitlinger ............................ 73/104
4,178,797 12/1979 Kozlowski ........................... 73/104

OTHER PUBLICATIONS

Strung, N., *An Encyclopedia of Knives*, J. B. Lippencott, Philadelphia & New York, 1976, p. 196.

Simmonds, T. G., *Wood Carving*, Bemrose & Sons, Ltd., London, p. 21 NK 9704 S592

*Primary Examiner*—S. Clement Swisher
*Attorney, Agent, or Firm*—W. M. Manning, Jr.

[57] ABSTRACT

A device for testing sharpness value of a cutting edge which includes an elongated body of a material into which a properly sharpened edge only will bite when lightly slid therealong at a predetermined angle. A sharply angled ridge is provided at at least one end of the body of the device and may be lightly drawn and/or pushed along the cutting edge to check for nicks or other imperfections in the edge. The edge tester is preferably of unitary construction, with a test ridge at both ends, and manufactured of a polymeric material. A method of testing the cutting edge is also disclosed and claimed.

17 Claims, 7 Drawing Figures

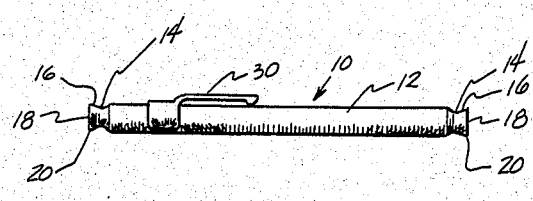
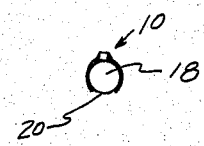
FIG. 1.   FIG. 2.
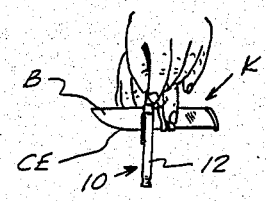
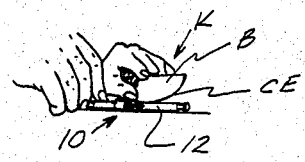
FIG. 3.   FIG. 4.
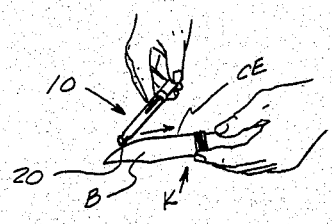
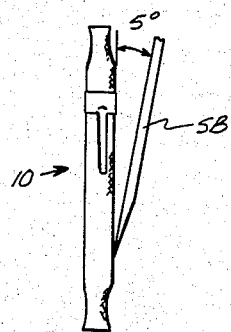
FIG. 5.
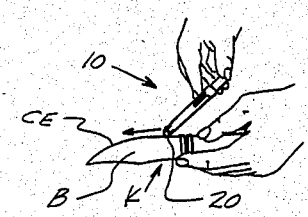
FIG. 7.
FIG. 6.

METHOD FOR TESTING THE SHARPNESS VALUE OF A CUTTING EDGE AND APPARATUS THEREFOR

BACKGROUND OF THE INVENTION

Cutting implements are in general subject to utilization by virtually every household and industry for the cutting or severing of an indeterminable number of items. In each environ, whether domestic, industrial or the like, quite obviously the task of one utilizing a cutting implement may be eased significantly if the particular cutting implement has a properly sharpened cutting edge. In the same vein, whereas many cutting implements found in use in industry are associated with a machine or other apparatus for effecting the cutting operation, likewise a better cut is realized with properly sharpened cutting edges.

Numerous and different techniques are being utilized for sharpening cutting edges. Generally speaking there has been no means available prior to the present invention for adequately determining the proper sharpness of a blade or cutting edge subsequent to the sharpening operation, short of use of the implement, per se. In other words, once a knife, chisel, cutting die or the like has been sharpened whether manually or by machine, it has generally been assumed that, following the sharpening operation, a proper cutting edge is present. Such is not, however a correct assumption. Due to improper sharpening techniques, misalignment of an edge with respect to a sharpening machine or the like, incorrectly sharpened edges may result, and while even following improper sharpening, a cutting edge may perform better for a limited period of time, such is not necessarily the case.

In many instances where improper cutting edges have been produced on a cutting implement, there is no real criticality to the need for a perfect cutting edge due to the short period of use of same by an individual, lack of criticality to the product being cut, or the like. Where, however, it is highly desirable, if not critical, that a proper cutting edge be continuously present for an implement for extended periods of time, then the need for a perfect cutting edge is paramount. In the meat cutting industry, for example, an individual utilizing an improperly sharpened knife will expend significantly greater amounts of energy in cutting the meat as opposed to one utilizing a blade with a proper cutting edge totally therealong. In such industry, for example, the employee will spend virtually all day with cutting meat, whereby the fatigue factor from utilizing an improperly sharpened instrument or knife can lead not only to extreme tiredness, but very importantly, also to reduced productivity. Also, in an industrial environ where the product being cut is critical as to the cut, per se, then likewise it is highly desirable if not absolutely necessary that a proper cutting edge be utilized to permit continuous production of first quality products.

By virtue of the method and apparatus of the present invention, one can quickly and accurately ascertain the sharpness value of a cutting edge. Hence, once the implement edge is sharpened, it can then be quickly determined, prior to utilization, whether a correct cutting edge is present along the entire length of the cutting surface. If defects are noted, corrective measures can be taken and the edge retested until a perfect edge results. The time required for testing and resharpening, if necessary, will invariably yield overall improvement.

While as mentioned above, the greatest need for the present invention is perhaps found in industry, same is likewise available for sportsmen, housewives, hobbyists, and the like.

There is no known prior that would anticipate or suggest the process or apparatus of the present invention.

SUMMARY OF THE INVENTION

It is an object of the present invention to provide a device that may be utilized to properly test the sharpness value of the cutting edge.

Another object of the present invention is to provide a hand held device that may be conveniently utilized by anyone in determining whether a proper cutting edge is present along the entire cutting surface of an implement.

Still further, another object of the present invention is to provide a device for determining the presence of a perfect cutting edge of a cutting implement.

Yet another object of the present invention is to provide a method for testing a cutting edge to accurately determine the value of the edge.

Still further, another object of the present invention is to provide a method by which the cutting value of any edge may be tested to accurately determine the sharpness of same while at the same time ascertaining the presence or absence of rough spots, nicks or other imperfections along the cutting edge.

Generally speaking, the device of the present invention for testing the sharpness value of a cutting edge comprises a body, said body including a smooth surface thereon of a material which when lightly contacted by a properly sharpened edge at a predetermined angular relationship, the edge will bite into same, while a dull edge sliding thereover under such conditions will not bite into same, said body further having at least one sharply angled ridge thereon that may be moved along said edge being tested to locate nicks and other imperfections in same.

Generally speaking, the method of determining the sharpness value of a cutting edge according to teachings of the present invention comprises the steps of bringing at least a predetermined portion of said edge into light angular sliding contact along a surface of a device having a characteristic that said portion of said edge will bite into said surface if properly sharpened and will slide over said surface if dull; drawing said edge across said surface to detect any rough spots therealong; and passing a sharp angled ridge lightly along said edge to detect any nicks and other imperfections in same.

More specifically, as to the device and method of the present invention, an elongated cylindrical polymeric device is preferably employed, and held in a generally vertical disposition with a portion of a cutting edge to be tested being brought into light angular sliding contact with the surface of same, preferably at an angle of about 45°. Due to the nature of the polymeric or other suitable material, a properly sharpened edge will bite into the surface of the cylindrical body whereas a dull edge or improperly sharpened edge will merely slide therealong. Once one portion of the edge has been tested in such fashion, adjacent edge portions may be tested, at, for example, one-half inch intervals, until the entire desired length of the cutting edge has been tested. Next, with the cylindrical body of the device disposed in a generally horizontal position, the cutting edge of the blade, generally in a vertical plane, may be brought into light sliding contact therewith. As the blade passes over the surface, any rough spots in the blade will be tactilely detected.

Once the roughness test has been conducted, the sharply angled ridge located, preferably at either end of the cylindrical body of the device may be passed along the surface of the cutting edge to detect the presence of nicks, or other imperfections in the cutting edge. In a preferred form, the angled ridge is defined by a reduced diameter body section tapering to an end of the body on one side and a generally flat end of the body on the other side. Preferably the sharply angled ridge is presented to the cutting edge with the device held at an angle of about 45° to the plane of the edge, and is pulled or drawn lightly along the entire length of the edge. Any nicks or imperfections will then be tactilely determined. Thereafter, with the device in a similar angular disposition with respect to the cutting edge, the ridge is moved in a reverse direction along the entire length of the cutting edge, very lightly and very slowly. Again nicks and imperfections in the edge will be tactilely located.

Assuming that the edge along its length properly bites into the surface of the device and that no rough spots, nicks or imperfections are detected therealong, a perfect cutting edge is present. Should, however, the cutting edge fail in any of the aforementioned test steps, then a proper approach would be to return to the sharpening process to alleviate the noted imperfection.

The above testing technique relates primarily to knives or other cutting instruments having a bevel on opposite sides of the cutting edge. When, however, it is desirable to test a single bevel blade such as wood chisels, plane blades, joiner blades, ice augers, chain saws, scissors, drill bits and the like, the same general procedures, as set forth above, may be followed with the exception that the angular relationship between the blade and the longitudinal test body is much less when the edge is moved along the longitudinal axis of the device in light contact therewith. Whereas with the double bevel blades, an angle of approximately 45° is preferred, with a single bevel blade, the blade is brought into angular sliding contact from a flat side as opposed to the bevel side, and at an angle of no more than about 5°.

BRIEF DESCRIPTION OF THE DRAWINGS

FIG. 1 is a plan view of an edge testing device according to teachings of the present invention.

FIG. 2 is an end view of the device as shown in FIG. 1.

FIG. 3 is an illustration of a preferred technique for testing the sharpness of a cutting edge utilizing the device illustrated in FIGS. 1 and 2.

FIG. 4 illustrates a preferred technique for determining the existence of rough spots along the surface of a cutting edge according to teachings of the present invention.

FIG. 5 and FIG. 6 illustrate preferred methods for testing a cutting edge for nicks or other imperfections according to teachings of the present invention.

FIG. 7 illustrates a preferred technique for determining sharpness of a single bevel cutting edge according to the present invention.

DESCRIPTION OF THE PREFERRED EMBODIMENTS

Making reference to the Figures, preferred embodiments of the present invention will now be described in detail. FIG. 1 illustrates a preferred device for testing the sharpness value of a cutting edge according to teachings of the present invention, generally indicated as 10. The edge tester 10 includes a body 12 that is preferably elongated and cylindrical in nature having reduced diameter sections 14 at opposite ends of same with a tapered section 16 extending from reduced diameter sections 14 to the terminal ends 18 of the device. Terminal ends 18 of device 10 present a surface that is approximately 90° with respect to the longitudinal axis of body 12, whereby a sharply angled ridge 20 is provided at opposite ends of body 12. Edge tester 10, in its preferred embodiment as illustrated is small and compact which permits virtually anyone to use same. In fact, a clip means 30 is received over body 12 which permits tester 10 to be conveniently carried in a pocket and thus remain readily available for use at all times.

The outer surface of body 12 must be of a material having a characteristic softness that a properly sharpened cutting edge, when lightly drawn across same in generally the disposition illustrated in FIG. 3, will bite into body 12. Exemplary of such surfaces are polymer surfaces, soft metals such as aluminum or brass, wood, or the like, though preferably the body is polymeric in nature, and most preferably a polyvinyl chloride composition.

While edge tester 10 according to the present invention is illustrated in its preferred form as a unitary structure of the same material, obviously the device could take numerous different forms. For example, though not shown, the outer surface and inner surface of body 12 could be manufactured of different materials. Likewise, a different material may be utilized for the sharply angled ridge at each end of the device.

Making reference to FIGS. 3 through 6, the method for testing the sharpness value of a double beveled cutting edge will now be described. As illustrated in FIG. 3, the edge tester 10 is held in one hand a vertically oriented position such that a knife generally K held in the other hand may present blade B at an angle of about 45° with respect to vertical. The cutting edge CE of blade B may then be brought into light sliding contact along the outer of body 12. FIG. 7 shows the relationship of the cutting edge to body 12 though at a much less angle. Should the knife cutting edge CE have a proper sharpness value, edge CE will bite into the outer surface of body 12, whereas a dull edge CE will not bite into body 12, but will simply side therealong. As illustrated in FIG. 3, only a small segment of cutting edge CE is being tested. Hence, once a particular segment or portion of cutting edge CE is so tested and passes the test, the procedure may be repeated for adjacent portions of the edge until all or a predetermined portion of cutting edge CE has been tested.

After evaluating the "biteability" of the particular cutting edge CE, the edge tester 10 may be rested in a horizontal disposition on a supporting surfaces (See FIG. 4). The cutting edge CE being tested, and preferably the full length of same, may then be lightly drawn across body 12. Pressure on body 12 other than the weight of knife K should be avoided, whereby any rough spots along the length of cutting edge CE will then be tactilely detected due to interruption of the smooth sliding action.

Once the roughness test illustrated in FIG. 4 has been conducted, knife K may then be held in the hand with the cutting edge CE facing upwardly (See FIG. 5). Edge tester 10 is then held at an angle of about 45° to vertical and sharply angled ridge 20 is lightly drawn along the entire length of edge CE. Any nicks or other imperfections in edge CE will be tactilely detected. Thereafter, as shown in FIG. 6, with tester 10 and knife K similarly located, ridge 20 is very lightly and very slowly pushed along the upwardly facing cutting edge CE likewise to tactilely detect the presence of nicks or other imperfections in edge CE.

While the testing steps illustrated in FIGS. 3 through 6 are shown and described in a particular sequence, obviously the steps may be performed in any desired order. During testing, should roughness, nicks or imperfections be detected, or should the knife not bite into the surface of body 12, an imperfect cutting edge is present. Testing should be interrupted at the point of detection of an imperfection and sharpening operation resumed to correct the noted problem. Retesting for the particular noted fault will then determine whether a proper resharpening has been accomplished, and testing can be resumed.

Testing of a cutting edge having one flat side and one bevel such as a chisel, scissors, and the like is, in most regards, like that described above. FIG. 7, however, illustrates a proper single bevel blade test which supplants the illustration of FIG. 3. When a single bevel blade SB is being tested as opposed to the double bevel blade type of FIG. 3, the angle of inclination is much less. Particularly, while double bevel blade surface is generally held at an angle of about 45° to the vertical, when testing a single bevel blade, an angle of no more than about 5° should be present. With the single bevel blade SB at the appropriate angle and the bevel facing away from tester 10 as illustrated in FIG. 7, a proper cutting edge will bite into body 12 of the test device 10, whereas a dull edge will simply slide therealong. After so testing the single bevel blade, the remaining test steps discussed with respect to FIGS. 4 through 6 may be performed to determine whether the cutting edge is proper and perfect, though again, the order of testing is not critical.

Though not shown herein, other devices may be tested for sharpness, such as for example fish hooks. One may drag a fish hook along body 12 of edge tester 10 in similar manner in which the hook would be drawn through the mouth of the fish. If the hook does not bite into body 12, chances are it will also not bite into the bony surface of the fish's mouth and should be resharpened.

Having described the present invention in detail, it is obvious that one skilled in the art will be able to make variations and modifications thereto. Accordingly, the scope of the present invention should be determined only by the claims appended hereto.

That which is claimed is:

1. A device for testing the sharpness value of a cutting edge comprising a body, said body including a smooth surface thereon of a material that will be penetrated by a properly sharpened edge brought into light angular contact therewith and will not be cut by a dull edge under such conditions, said body further having at least one sharply angled ridge thereon that may be moved along said edge being tested to locate nicks and other imperfections in same; and wherein said at least one sharply angled ridge is located at a terminal end of said body and wherein said body defines a reduced diameter section adjacent said sharply angled ridge.

2. The device as defined in claim 1 wherein said body is a longitudinal and is cylindrical cross section.

3. The device as defined in claim 2 wherein said body is manufactured from said cuttable material, whereby substantially all surfaces of same may be used for testing sharpness of said edge.

4. The device as defined in claim 1 wherein said body tapers outwardly from said reduced diameter section to said sharply angled ridge.

5. The device as defined in claim 1 wherein said body is manufactured of a polymeric material.

6. The device as defined in claim 1 wherein said body is manufactured of a soft metal.

7. The device as defined in claim 1 wherein said body is manufactured of wood.

8. The device as defined in claim 1 wherein a sharp angled ridge is provided at opposite ends of said body.

9. A device for testing the sharpness value of a cutting edge comprising an elongated, cylindrical polymeric body, said body presenting smooth surfaces therealong which permit a properly sharpened edge to bite into same when said edge is brought into light angular sliding contact therewith while a dull edge will slide thereover, said body further having at least one reduced diameter section adjacent an end of same and a tapered section from said reduced diameter section to said end, defining a sharply angled ridge that may be moved along said edge being tested to test said edge for nicks and other imperfections.

10. The device as defined in claim 8 wherein an end of said body presents a surface at an angle of about 90 degrees with respect to surfaces along a major length of said body whereby a side of said ridge opposite said reduced diameter section is generally flat.

11. The device as defined in claim 9 wherein one said sharply angled ridge is provided at each end of said body.

12. A method of testing sharpness value of a cutting edge comprising the steps of:
(a) bringing at least a predetermined portion of said edge into light angular sliding contact along a surface of a device having a characteristic that said portion of said edge will bite into said surface if properly sharpened and will side over said surface if dull, said device being an elongated cylindrical polymeric device;
(b) drawing said edge across said surface to detect any rough spots therealong; and
(c) passing a sharp angled ridge of said device lightly along said edge to detect any nicks or other imperfections in same.

13. The method as defined in claim 12 wherein said sharply angled ridge is held at about 45 degrees as it is passed in light contact along said edge.

14. The method as defined in claim 12 wherein said ridge is both pulled along said edge and pushed along said edge in an opposite direction.

15. The method as defined in claim 12 wherein step (a) is repeated from adjacent portions of said edge, fully along the cutting edge.

16. The method as defined in claim 12 wherein a single beveled edge is being tested and said edge is brought into light sliding contact with said surface at an angle of not more than about 5 degrees from vertical.

17. The method as defined in claim 12 wherein a double beveled edge is being tested and said edge is brought into light sliding contact with said surface at an angle of about 45 degrees from vertical.

* * * * *

UNITED STATES PATENT OFFICE
CERTIFICATE OF CORRECTION

Patent No. 4,528,843           Dated July 16, 1985

Inventor(s)  John C. Juranitch

It is certified that error appears in the above-identified patent and that said Letters Patent are hereby corrected as shown below:

Column 2, line 7, after "prior", please insert --art--.

Column 4, line 54, please change "side" to --slide--.

In the claims:

Column 6, line 44, change "side" to --slide--.

Signed and Sealed this

First Day of October 1985

[SEAL]

Attest:

Attesting Officer

DONALD J. QUIGG

Commissioner of Patents and
Trademarks—Designate